(12) United States Patent
Park et al.

(10) Patent No.: US 8,727,985 B2
(45) Date of Patent: May 20, 2014

(54) MEDICAL SYSTEM FOR PROVIDING EXTERNAL TRIGGER SIGNAL

(75) Inventors: Sang Hyun Park, Seoul (KR); Chul An Kim, Seoul (KR)

(73) Assignee: Medison Co., Ltd, Kangwon-Do (KR)

( * ) Notice: Subject to any disclaimer, the term of this patent is extended or adjusted under 35 U.S.C. 154(b) by 407 days.

(21) Appl. No.: 12/643,782

(22) Filed: Dec. 21, 2009

(65) Prior Publication Data

US 2010/0305425 A1 Dec. 2, 2010

(30) Foreign Application Priority Data

Jun. 1, 2009 (KR) ........................ 10-2009-0048156

(51) Int. Cl.
*A61B 8/00* (2006.01)
(52) U.S. Cl.
USPC ........... 600/437; 600/439; 600/441; 600/443; 345/653
(58) Field of Classification Search
USPC .................. 600/437, 439, 441, 443; 345/653
See application file for complete search history.

(56) References Cited

U.S. PATENT DOCUMENTS

| 6,350,238 | B1 | 2/2002 | Olstad et al. |
| 2006/0119623 | A1* | 6/2006 | Quigley ........................ 345/653 |
| 2006/0291615 | A1 | 12/2006 | Nishide et al. |
| 2009/0192386 | A1* | 7/2009 | Hashimoto ................... 600/443 |

FOREIGN PATENT DOCUMENTS

| KR | 10-2001-0060238 A | 7/2001 |
| KR | 10-2006-0135560 A | 12/2006 |
| KR | 10-2008-0011743 A | 2/2008 |

OTHER PUBLICATIONS

Korean Office Action issued in Korean Patent Application No. KR 10-2009-0048156 dated Sep. 16, 2011.

* cited by examiner

*Primary Examiner* — Joel Lamprecht
(74) *Attorney, Agent, or Firm* — McDermott Will & Emery LLP

(57) ABSTRACT

There are disclosed embodiments for a medical system capable of providing an external trigger signal. The medical system comprises at least one of an ECG signal providing unit to provide an ECG signal indicative of an electrical change in a target object, a reference signal providing unit to provide at least one reference signal for triggering an operation of the medical system, and a medical image providing unit to provide a medical image of the target object. The medical system may further comprise a processor to form an external trigger signal using at least one of the ECG signal, reference signal and medical image. The medical system may further comprise a signal interface unit to transmit the external trigger signal to an external device coupled to the medical system.

6 Claims, 2 Drawing Sheets

MEDICAL SYSTEM FOR PROVIDING EXTERNAL TRIGGER SIGNAL

CROSS-REFERENCE TO RELATED APPLICATIONS

The present application claims priority from Korean Patent Application No. 10-2009-0048156 filed on Jun. 1, 2009, the entire subject matter of which is incorporated herein by reference.

TECHNICAL FIELD

The present disclosure relates to medical systems, and more particularly to a medical system for providing an external trigger signal.

BACKGROUND

With the development of sophisticated electronic devices, many medical systems, which can obtain images of human internal organs, have been recently introduced. Among such medical systems, an ultrasound system has been extensively used for acquiring internal information of a target object due to its non-invasive and non-destructive nature. Since the ultrasound system may provide a high resolution image without any surgical treatment, it has proven to be very helpful in the medical profession.

However, the conventional ultrasound system has a problem since it is difficult to synchronize an ultrasound system with an external device coupled thereto and accurately recognize operating conditions of the ultrasound system (e.g., whether or not an ultrasound signal has been transmitted, whether or not a medical image has been formed, etc.).

SUMMARY

Embodiments of a medical system adapted to provide an external trigger signal for synchronizing with an external device and informing the external device of operating condition and timing of the medical system are disclosed herein. In one embodiment, by way of non-limiting example, the medical system of the present invention comprises: an ECG signal providing unit operable to provide an ECG signal indicative of an electrical change in a target object; a processor operable to form an external trigger signal using the ECG signal; and a signal interface unit operable to transmit the external trigger signal to an external device coupled to the medical system.

In one embodiment, the medical system of the present invention comprises: a medical image providing unit operable to provide a medical image of a target object; a processor operable to form an external trigger signal using the medical image; and a signal interface unit operable to transmit the external trigger signal to an external device coupled to the medical system.

In one embodiment, the medical system of the present invention comprises: a reference signal providing unit operable to provide at least one reference signal for triggering an operation of the medical system; a processor operable to form an external trigger signal using at least one reference signal; and a signal interface unit operable to transmit the external trigger signal to an external device coupled to the medical system.

In one embodiment, the medical system of the present invention comprises: an ECG signal providing unit operable to provide an ECG signal indicative of an electrical change in a target object; a medical image providing unit operable to provide an image of a target object; a reference signal providing unit operable to provide a reference signal for triggering an operation of the medical system; a processor operable to form an external trigger signal using at least one of the ECG signal, the medical image and the reference signal; and a signal interface unit operable to transmit the external trigger signal to an external device coupled to the medical system.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. While in the following description, an ultrasound system will be discussed as an example of a medical system for the convenience of explanation, it should be appreciated that the present invention may be applied to any medical system capable of providing a medical image such as a computed tomography (CT) device, a magnetic resonance imaging (MRI) device, an X-ray device, etc. One of ordinary skill in the art will appreciate that the following description is illustrative only and is not in any way limiting. Other embodiments of the present invention may readily suggest themselves to such skilled persons having the benefit of this disclosure.

Figure 1:
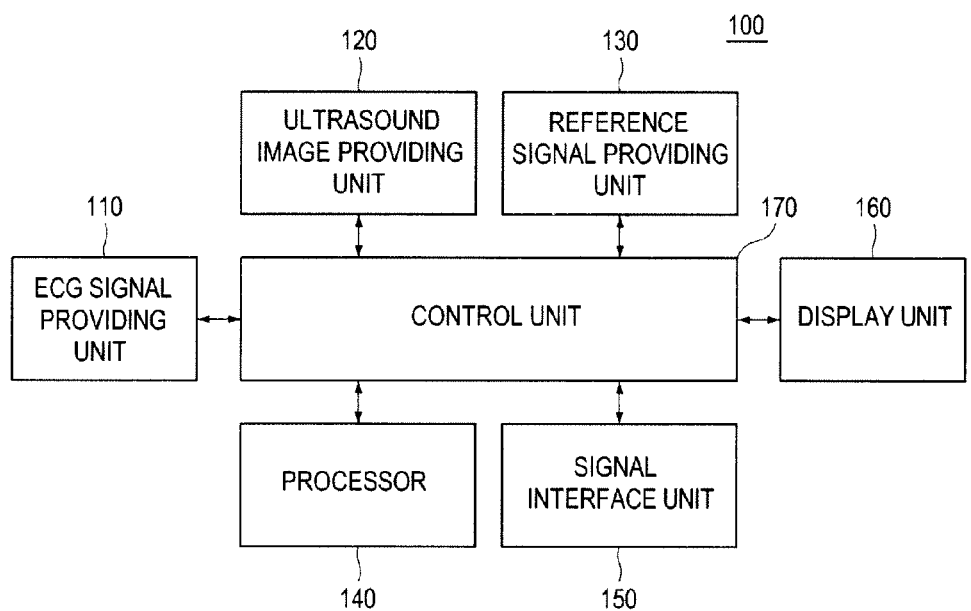
FIG. 1 is a block diagram showing an illustrative embodiment of an ultrasound system.

FIG. 1 is a block diagram showing an illustrative embodiment of an ultrasound system. The ultrasound system 100 comprises an electrocardiogram (ECG) signal providing unit 110 configured to form an ECG signal from a subtle electrical change caused by contraction and relaxation of an object of interest (e.g., heart, myocardium) in the target object.

The ultrasound system 100 may further comprise an ultrasound image providing unit 120. The ultrasound image providing unit may be operable to transmit an ultrasound signal to the target object, receive the ultrasound signal reflected from the target object (i.e., ultrasound echo signal), and form an ultrasound image of the target object based on the received echo signal. The ultrasound image may include a B-mode (brightness mode) image, an M-mode (motion mode) image, a doppler mode image, a color mode image and an elastic mode image, although it is certainly not limited thereto. The ultrasound system 100 may further comprise a user input unit (not shown) that may be implemented as a control panel, a mouse, a keyboard, etc., to allow a user to input instructions.

Figure 2:
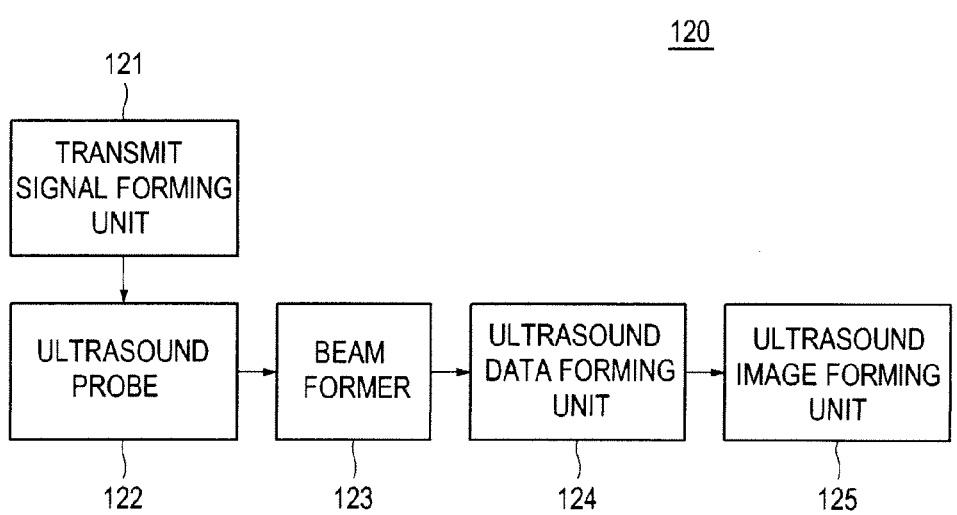
FIG. 2 is a block diagram showing an illustrative embodiment of an ultrasound image providing unit.

FIG. 2 is a block diagram showing an illustrative embodiment of the ultrasound image providing unit 120. The ultrasound image providing unit 120 may include a transmit signal forming unit 121, a ultrasound probe 122 including a plurality of transducer elements, a beam former 123, a ultrasound data forming unit 124, and a ultrasound image forming unit 125.

The transmit signal forming unit 121 may be operable to form a transmit signal to be applied to each of the transducer elements of the ultrasound probe 122. By way of a non-limiting example, the positions and focusing points of the transducer elements of the ultrasound probe 122 may be considered in forming the transmit signal. In one embodiment, the transmit signal may include a transmit signal for acquiring frames of an ultrasound image.

Figure 3:
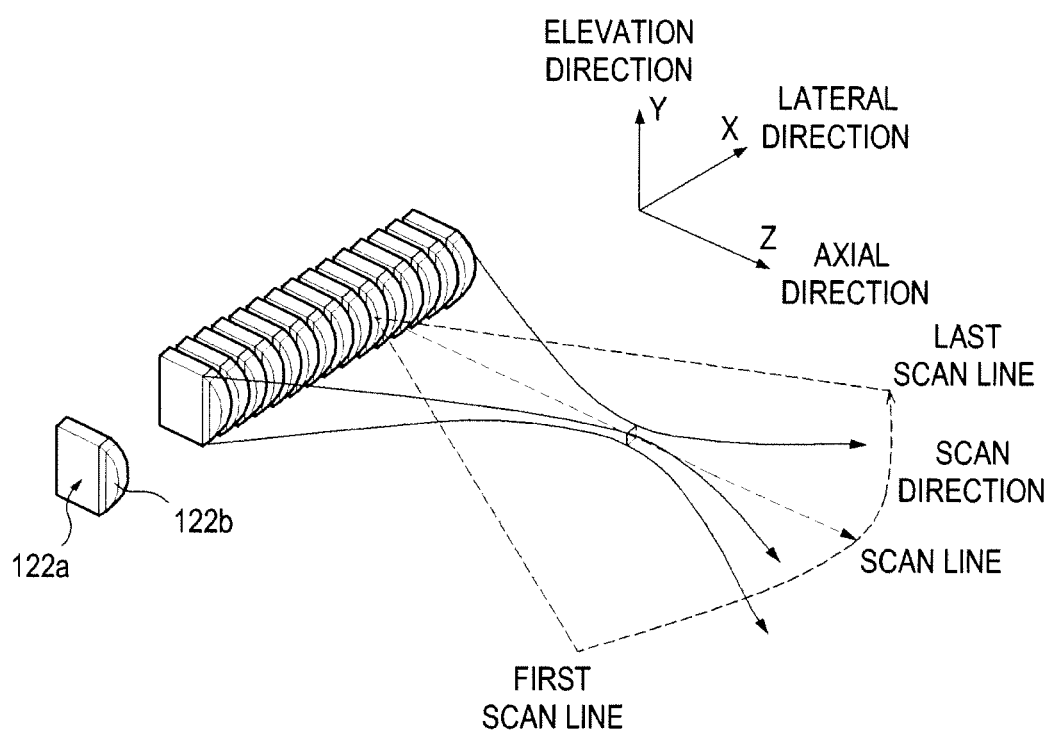
FIG. 3 is a schematic diagram showing an example of a transducer element, a scanning line and a coordinate system.

The ultrasound probe 122 may operate to convert the transmit signal provided by the transmit signal forming unit 121 into an ultrasound signal and transmit it to the target object. The ultrasound probe 122 may further operate to receive the ultrasound echo signal reflected from the target object and form a receive signal. The ultrasound probe 122 may include a plurality of transducer elements 122a operable to convert an ultrasound signal and an electrical signal reciprocally, as illustrated in FIG. 3. The ultrasound signal, which is transmitted from each of the transducer elements 122a, constitutes an ultrasound beam to be sent to the target object along a plurality of scan lines, as illustrated in FIG. 3. In FIG. 3, the plurality of transducer elements 122a are depicted in the rectangular coordinate system constituted by the lateral direction, axial direction and elevation direction, all of which are perpendicular to each other. In one embodiment, the ultrasound probe 122 may include a plurality of acoustic lenses 122b.

The beam former 123 may be configured to form a digital signal through analog-to-digital conversion of the receive signal provided by the ultrasound probe 122. The beam former 123 may perform receive-focusing upon the digital signal in consideration of the positions and focusing points of the transducer elements 122a, and form a receive-focused signal thereby.

The ultrasound data forming unit 124 may be configured to form ultrasound data of the target object using the receive-focused signal provided by the beam former 123. In one embodiment, the ultrasound data forming unit 124 may perform various signal processing (e.g., gain adjustment, filtering) required for forming the ultrasound data.

The ultrasound image forming unit 125 may be configured to form an ultrasound image of the target object using the ultrasound data provided by the ultrasound data forming unit 124. The ultrasound image forming unit 125 may be further configured to form an ultrasound image that is synchronized with the ECG signal provided by the ECG signal providing unit 110.

Referring back to FIG. 1, the ultrasound system 100 may further comprise a reference signal providing unit 130 that is configured to form a reference signal for triggering the operation of the ultrasound system 100. In one embodiment, the reference signal may include a first reference signal for triggering the operation of transmitting the ultrasound signal to the target object and a second reference signal for triggering the operation of forming the ultrasound image using the ultrasound data. Although in the aforementioned embodiment, the reference signal providing unit has been explained as forming two kinds of reference signals, the present invention is not limited thereto. For example, the ultrasound system 100 may be configured to set the reference signal providing unit 130 to form an additional reference signal in response to a user input. Alternatively, the ultrasound system 100 may provide a menu indicating various reference signals that prompt the user to select at least one of the available reference signals.

The ultrasound system 100 may further comprise a processor 140 configured to form an external trigger signal, which is provided to an external device (not shown) coupled to the ultrasound system 100. In one embodiment, the processor 140 may be configured to analyze the ECG signal provided by the ECG signal providing unit 110, and based on the analysis, form the external trigger signal each time a predetermined ECG signal pattern is detected. In one embodiment, the predetermined ECG signal pattern may include heart rhythms (e.g., contraction period, relaxation period). In another embodiment, the processor may be configured to analyze the ultrasound image provided by the ultrasound image providing unit 120, and based on the analysis, form the external trigger signal each time a predetermined ultrasound image pattern is detected. In one embodiment, the predetermined ultrasound image pattern may include backflow of blood in a color Doppler mode image, blood flow velocity and peak interval in a Doppler mode image, and lesions of a B-mode and elastic image. In one embodiment, the ultrasound image pattern may be set by a user input. In another embodiment, the processor 140 may be configured to form the external trigger signal each time the reference signal is provided by the reference signal providing unit 130. In yet another embodiment, the processor 140 may be configured to form the external trigger signal using at least one of the ECG signal, the ultrasound image and the reference signal.

The ultrasound system 100 may further comprise a signal interface unit 150 configured to transmit the external trigger signal provided by the processor 140 to the external device. The signal interface unit 150 may be implemented with any type of communication interface that enables communication with the external device.

The ultrasound system 100 may further comprise a display unit 160 to display the ultrasound image provided by the ultrasound image providing unit 120 and the ECG signal (ECG waveform), which is provided by the ECG signal providing unit 110. In one embodiment, the display unit 160 may include a liquid crystal display (LCD), a cathode ray tube (CRT) or any other device capable of displaying an image.

The ultrasound system 100 may further comprise a control unit 170 that interfaces with other elements of the ultrasound system 100 to control the functions thereof. By way of non-limiting example, the control unit 170 may be configured to supervise transmission/reception of the ultrasound signal, formation/provision of the ultrasound image, formation/provision of the ECG and reference signals, and formation/transmission of the external trigger signal.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements within the scope of the disclosure, the drawings and the appended claims. In addition to variations and modifications in the component parts and/or arrangements, alternative uses will also be apparent to those skilled in the art.

What is claimed is:

1. An ultrasound system, comprising:
an ultrasound image provider configured to provide an ultrasound image of a target object;
a processor configured to analyze the ultrasound image and form an external trigger signal including information on an operating condition and an operating timing of the ultrasound system when a predetermined pattern is detected based on a result of the analysis; and
a signal interface unit configured to transmit the external trigger signal to the external device coupled to the ultrasound system,
wherein the ultrasound system is synchronized with the external device based on the external trigger signal.

2. The ultrasound system of claim 1, further comprising:
an ECG signal provider configured to provide an ECG signal indicative of an electrical change in the target object.

3. The ultrasound system of claim 2, wherein the processor is further configured to analyze the ECG signal and form the external trigger signal each time a predetermined ECG signal pattern is detected.

4. The ultrasound system of claim 1, further comprising:
a reference signal provider configured to provide a reference signal for triggering an operation of the ultrasound system; and
an ultrasound data former configured to form ultrasound data of the target object.

5. The ultrasound system of claim 4, wherein the reference signal includes:
a first reference signal for triggering an operation of transmitting an ultrasound signal to the target object; and
a second reference signal for triggering an operation of forming the medical image using the ultrasound data.

6. The ultrasound system of claim 4, wherein the processor is further configured to form the external trigger signal each time the reference signal is provided by the reference signal provider.

* * * * *